(12) United States Patent  (10) Patent No.: US 6,398,810 B1
Surprise  (45) Date of Patent: Jun. 4, 2002

(54) BREAST PROSTHESIS

(76) Inventor: Evelyn M. Surprise, P.O. Box 451, Cedar Lake, IN (US) 46303

( * ) Notice: Subject to any disclaimer, the term of this patent is extended or adjusted under 35 U.S.C. 154(b) by 0 days.

(21) Appl. No.: 09/499,994

(22) Filed: Feb. 8, 2000

(51) Int. Cl.$^7$ .................................................. A61F 2/52
(52) U.S. Cl. ..................... 623/7; 128/112.1; 128/117.1; 128/120.1
(58) Field of Search ........................... 623/7; 128/112.1, 128/117.1, 120.1

(56) References Cited

U.S. PATENT DOCUMENTS

| | | | |
|---|---|---|---|
| 3,641,592 A | 2/1972 | Bleyekr | 3/36 |
| 3,706,104 A | 12/1972 | Dehlin et al. | 3/36 |
| 3,807,412 A | 4/1974 | Connelly | 128/481 |
| 3,811,133 A | 5/1974 | Harris | 3/36 |
| 4,011,611 A | 3/1977 | Lederman | 5/361 B |
| 4,071,914 A | 2/1978 | Silverman | 3/36 |
| 4,828,559 A | 5/1989 | Greenberg | 623/7 |

OTHER PUBLICATIONS

Classique® Post–Mastectomy Needs, Natural–Looking Classique® Prostheses and Spenco® Soft Breast Forms and Bras; Sears Healthcare Catalog, 1992–1993.
We Help Make Life Beautiful Again brochure, AMOENA®, ©1996 Coloplast Corp.

*Primary Examiner*—Corrine McDermott
*Assistant Examiner*—Choon P. Koh
(74) *Attorney, Agent, or Firm*—Nawrocki, Rooney & Sivertson, P.A.

(57) ABSTRACT

A breast form receivable in the cup of a brassiere includes a breathable padded casing selectively filled with a flowable aggregate so as to substantially and comfortably conform to the chest cavity of a wearer, thereby being responsive to the movements of the wearer. The breathable padded casing includes a plurality of soft and supple composite panels joined together so as to loosely confine the flowable aggregate and thereby provide a soft but firm appearance for the breast form.

5 Claims, 1 Drawing Sheet

BREAST PROSTHESIS

TECHNICAL FIELD

The present invention relates to a breast prosthesis, and more particularly to a breast prosthesis receivable in the cup of a brassiere that simulates the look and feel of the removed breast so as to be responsive to a woman's everyday movements, and which is comfortable against the chest wall with softness, yet is durable enough to be repeatedly washed and dried.

BACKGROUND OF INVENTION

Hundreds of thousands of women annually undergo mastectomy surgery. As can be appreciated, a woman suffers severe physiological and psychological trauma following such surgery. Restoration to a pre-surgery appearance and feel is critical in overcoming both feelings of physical imbalance and the severe emotional shock at the apparent loss of part of their femininity. Restorative options include reconstructive surgery (i.e., implants introduced into the chest cavity, whether artificial or comprising the patient's own tissue) or breast forms.

Breast forms are prostheses worn externally to simulate the natural contours and weight of a breast. Generally the forms are symmetrical for use on either side of the body (e.g., tri-corner, teardrop or heart shape) or are asymmetrical for side specific (i.e., right or left) use (e.g., curved teardrop or extended triangle). Traditionally breast forms have been made from silicone, foam or fiberfill and have been worn in specially fitted post-mastectomy brassieres which have included a stitched pocket or other means to hold the form in place, usually in a particular alignment or desired orientation. Some heretofore known breast, forms are affixable directly to the chest cavity using adhesives formulated for such purposes, while others are received in the cup of a standard brassiere (i.e., a brassiere not especially modified to receive and retain a breast form).

Heretofore, breast forms have been difficult to fit properly, let alone comfortably, and have moved and shifted around during use, causing considerable embarrassment. In some cases, the artificial breast has not maintained the proper shape and has appeared out of line or in a different shape than the other natural breast. In other cases, the breast form has been hot and uncomfortable to wear (i.e., sticking to or otherwise irritating the chest wall), even for short periods of time. Although attempts have been made at providing weighted and cushioned breast forms, common shortcomings include forms that are too hard, such that engagement may create an acute or chronic discomfort, and/or forms that are too heavy and contribute to feelings of physical imbalance. As a majority of the breast forms cannot be laundered, or at, least have been difficult to wash and dry, replacement at: frequent intervals is sometimes necessary, and such replacement, whether it be driven by wear considerations or weight gain/loss of the wearer, as often is the case, can be costly, even to the point of being cost prohibitive. In still other cases, the filling of the breast form is rigidly structured, thereby contributing to a solid, stationary and often times an unnatural appearance for the breast form.

SUMMARY OF THE INVENTION

The present invention provides a breast form having a non-structured filling which responds to a woman's everyday movements thereby contributing to a balanced feel and natural appearance. The breast form is receivable in the cup of a brassiere and comprises a breathable padded casing selectively filled with a flowable aggregate so as to substantially and comfortably conform to the chest cavity of a wearer, thereby being responsive to the movements of the wearer. The breathable padded casing in turn comprises a plurality of soft and supple composite panels joined together so as to loosely confine the flowable aggregate. In a preferred embodiment, each of the soft and supple composite panels of the plurality of soft and supple composite panels has interior and exterior layers separated by a cushioning intermediate layer. The panels generally provide a soft but firm appearance for the breast form.

More specific features and advantages will become apparent with reference to the DETAILED DESCRIPTION OF THE INVENTION, appended claims, and the accompanying drawing figures.

DETAILED DESCRIPTION OF THE INVENTION

Figure 1:
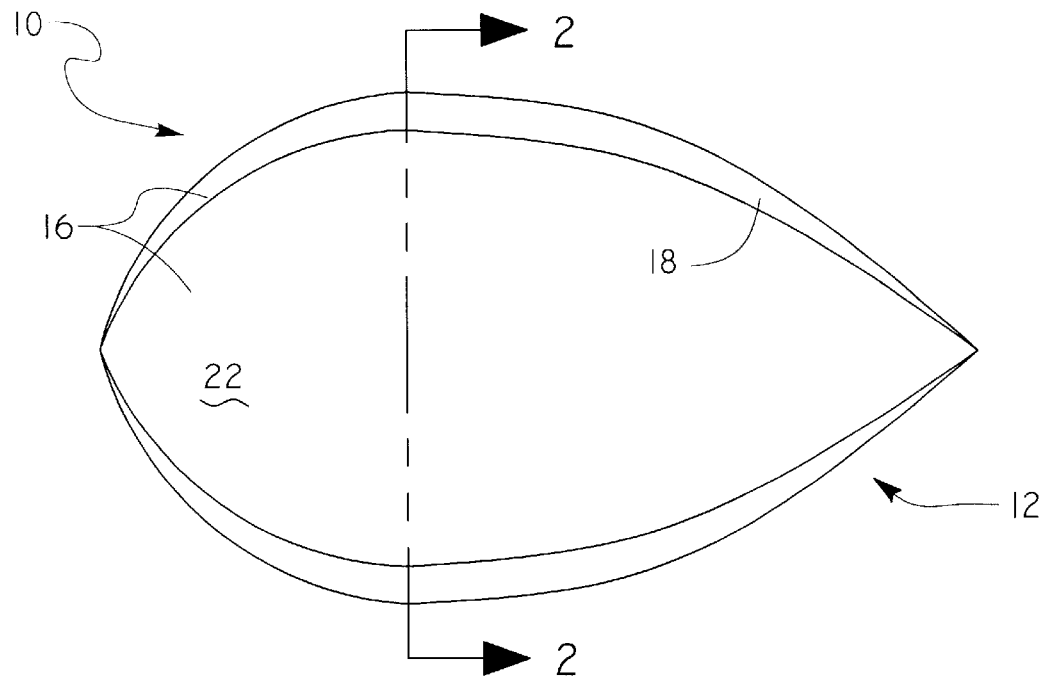
FIG. 1 is a side elevational representation of the breast form of the present invention.
Figure 2:
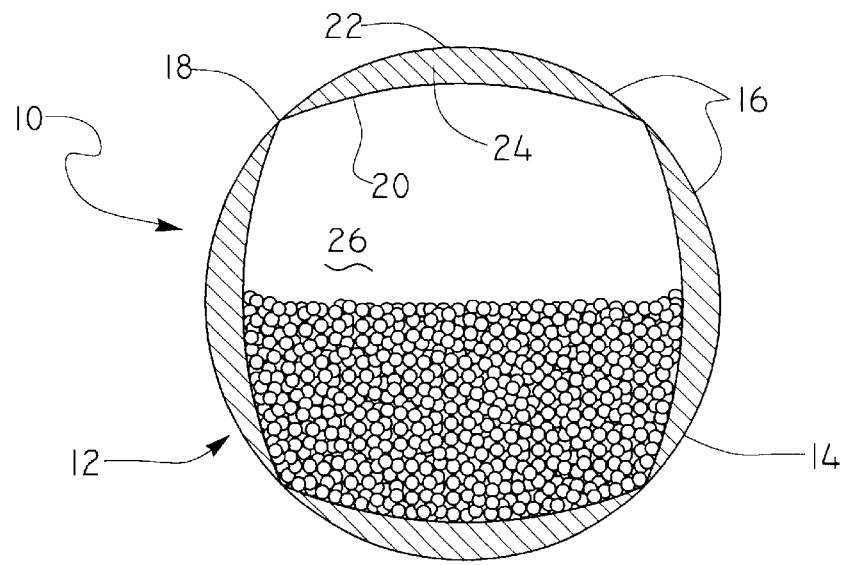
FIG. 2 is a sectional view along line 2—2 of FIG. 1, particularly illustrating the panels of the casing and the flowable aggregate contained therein.

Referring to FIGS. 1 and 2, a tear drop shaped breast form 10 is shown having a breathable padded casing 12 selectively filled with a flowable aggregate 14. Other breast form shapes incorporating the salient features hereof are likewise contemplated. The padded casing 12 includes a plurality of soft and supple composite panels or sections 16 joined together so as to loosely confine the flowable aggregate 14. Preferably four such panels 16 sewn together, or otherwise joined about their outer marginal edges 18, comprise the casing 12, with variations possible without deviating from the scope of the subject invention. Each of the soft and supple composite panels 16 are ideally identical in their configuration and construction, having interior 20 and exterior 22 layers spaced apart by a cushioning intermediate layer 24 that provides a degree of body or form for the panel 16. Aside from forming the casing 12, the panels 16 provide a soft but firm appearance for the breast form 10 and aid in replicating the free movement of a natural breast, as by the responsive flexing of adjoining panels of the casing.

The composite panels 16 of the breathable padded casing 12 are constructed so as to be soft and supple, moisture vapor transmitting—so as to avoid feeling hot and sticky—and able to withstand repeated washing and drying over a prolonged period of use. Furthermore, the composite panel design permits the breast form of the subject invention to adapt itself to brassiere cups of varying configurations of the numerous brassieres available in the marketplace.

The exterior layer 22 of the composite panels 16 are preferably formed from muslin, a fine delicately woven cotton fabric. Muslin does an exceptional job at absorbing perspiration, providing softness, frictionally interfacing with the cup of a brassiere in which it is received, and rendering the casing 12 such that it is able to be easily cared for. Blends of cotton and polyester fibers yield a wash-n-wear fabric which is soft, porous, adequate in frictional character, moisture absorbent and moisture transmissive. The interior layer 24 of the composite panels 16 (i.e., the "backing" for the cushioning intermediate layer) is preferably, but not necessarily, formed as the exterior layer 22, from muslin or other like material, as some economical advantage is generally obtained in using identical material for the interior and exterior layers.

The cushioning intermediate layer 24 of the soft and supple composite panels 16 are preferably formed from padding material such as bound cotton batting. First and foremost this cushioning intermediate layer 24 provides each of the composite panels 16 with a measure of form or body sufficient to provide the breast form 10 with a firm yet soft responsive look as the flowable aggregate 14 shifts in response to a wearer's actions/motions. Furthermore, the intermediate layer 24 is of such a character so as to provide the breast form 10 with a visually smooth, homogenous exterior surface (i.e., it conceals from view any bumps, lumps or other unnatural features attributable to the flowable aggregate and its nature). It is, further, advantageous in that the cushioning intermediate layer 24 has properties not inconsistent with those of the exterior layer 24 (namely that it be soft, porous, moisture absorbent and moisture transmissive).

The padded casing 12 of the breast form 10 is selectively filled with flowable aggregate 14 such that the breast form 10 is sized so as to be consistent with available brassiere cup sizes. It is important that sufficient void space 26 remain in the filled padded casing 12 so as to thereby permit the flow or shifting of the flowable aggregate 14 therein. Preferably the casing 12 should be filled with flowable aggregate to between about 60 and 80% of casing capacity, and seldomly filled beyond 90% of the casing capacity.

The flowable aggregate 14 contained in the padded casing or sack 12 is substantially and comfortably conforming to the chest cavity of a wearer, and the brassiere cup into which it is received. As such, it is responsive to the everyday movements and motions of the wearer. The flowable aggregate 14, shifting in response to the wearer's movements, provides a responsive flexibility unlike heretofore-known breast forms which are rigid, semi-rigid or even resilient, and that are in all events structured. Among further benefits of the unstructured filling are that the breast form of the subject invention need not be specially fit, thus avoiding the potential embarrassment and or distress sometimes accompanying such a task, and the pain associated with a structured breast form pressing against the chest cavity is eliminated as the flowable aggregate responds to such pressure.

Preferably the flowable aggregate comprises polyester elements in the form of either pellets, disks, curved cylinders, etc. Preferably the flowable aggregate has a substantially uniform size distribution to support the natural and uniform appearance of the breast form generally. The polyester elements provide weight and cushion for the breast form of the subject invention without being hard or heavy, as is the case, for instance, with prior art uses of BB's, buck shot, sinkers etc. Furthermore, the polyester elements are not a hindrance or obstacle to repeated washing and drying of the breast form.

Among further benefits of the subject breast form is its elegant simplicity which translates into relatively low production costs. As a matter of fact, whether due to weight gain, weight loss, or the aging process, a woman's breast size changes, necessitating at some point in time replacement of a mismatched breast form. Heretofore this had been an expensive proposition, one bordering on a luxury.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A breast form receivable in the cup of a brassiere comprising a breathable padded casing selectively filled with a flowable aggregate so as to substantially and comfortably conform to the chest cavity of a wearer and being responsive to the movements of the wearer, said breathable padded casing comprising a plurality of soft and supple composite panels joined together so as to loosely confine said flowable aggregate, wherein each of said soft and supple composite panels has an interior and an exterior layer separated by a cushioning intermediate layer, said panels providing a soft but firm appearance for said breast form.

2. A breast form receivable in the cup of a brassiere comprising a breathable padded casing selectively filled with a flowable aggregate so as to substantially and comfortably conform to the chest cavity of a wearer and being responsive to the movements of the wearer, said breathable padded casing comprising a plurality of soft and supple composite panels joined together so as to loosely confine said flowable aggregate, wherein each of said soft and supple composite panels is identically configured, said panels providing a soft but firm appearance for said breast form.

3. The breast form of claim 1 wherein said exterior layer of each of said panels comprises muslin.

4. The breast form of claim 1 wherein said intermediate layer of each of said panels comprises padding.

5. The breast form of claim 4 wherein said padding is bound cotton batting.

\* \* \* \* \*